(12) United States Patent
Dal Farra et al.

(10) Patent No.: US 7,842,670 B2
(45) Date of Patent: Nov. 30, 2010

(54) COSMETIC AND PHARMACEUTICAL COMPOUNDS FOR INDUCING THE SYNTHESIS OF SIRT PROTEINS IN SKIN AND METHODS OF USE THEREOF

(75) Inventors: Claude Dal Farra, Kerhonkson, NY (US); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 220 days.

(21) Appl. No.: 11/910,098

(22) PCT Filed: Mar. 30, 2006

(86) PCT No.: PCT/EP2006/003190

§ 371 (c)(1),
(2), (4) Date: Sep. 28, 2007

(87) PCT Pub. No.: WO2006/103110

PCT Pub. Date: Nov. 5, 2006

(65) Prior Publication Data

US 2009/0082278 A1 Mar. 26, 2009

(30) Foreign Application Priority Data

Apr. 1, 2005 (FR) .................................. 05 03202

(51) Int. Cl.
*A61K 38/00* (2006.01)
(52) U.S. Cl. .......................................... 514/14; 514/16
(58) Field of Classification Search ....................... None
See application file for complete search history.

(56) References Cited

U.S. PATENT DOCUMENTS

2003/0064411 A1 * 4/2003 Herath et al. ................ 435/7.2

FOREIGN PATENT DOCUMENTS

WO 2005002555 1/2005
WO WO2006081329 * 8/2006

OTHER PUBLICATIONS

Porcu M et al: "The emerging therapeutic potential of sirtuin-interacting drugs: from cell death to lifespan extension" Trends in Pharmacological Sciences, Elsevier, Hayworth, GB, vol. 26, No. 2, Feb. 2005, pp. 94-103, XP004727629 ISSN: 0165-6147 the whole document.

* cited by examiner

*Primary Examiner*—Robert Landsman
(74) *Attorney, Agent, or Firm*—Young & Thompson

(57) ABSTRACT

A cosmetic dermo-pharmaceutical, or dermatological composition having as an active agent in an acceptable cosmetic or pharmaceutical medium, at least one compound able to activate the synthesis or SIRT proteins in skin cells.

13 Claims, No Drawings

```
                        SEQUENCE LISTING

<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(3)
<223> OTHER INFORMATION: This region may encompass 0 to 3 variable amino
      acid residues
<220> FEATURE:
<221> NAME/KEY: MOD_RES
<222> LOCATION: (11)..(13)
<223> OTHER INFORMATION: This region may encompass 0 to 3 variable amino
      acid residues

<400> SEQUENCE: 1

Xaa Xaa Xaa Gly Leu Tyr Asp Asn Leu Glu Xaa Xaa Xaa
  1               5                  10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2
```

-continued

```
Gly Leu Tyr Asp Asn Leu Glu
 1               5
```

COSMETIC AND PHARMACEUTICAL COMPOUNDS FOR INDUCING THE SYNTHESIS OF SIRT PROTEINS IN SKIN AND METHODS OF USE THEREOF

The invention relates to the cosmetic and pharmaceutical fields, particularly the field of dermatology. The present invention concerns a cosmetic, or dermo-pharmaceutical, or dermatological composition comprising, as an active agent in an acceptable cosmetic or pharmaceutical medium, at least one compound able to activate the synthesis of SIRT proteins in skin cells. The present invention also relates to the use of said composition.

The skin is a protective organ that covers the totality of the body's surface. It is a vital organ ensuring multiple sensitive and protective functions against external immunobiological, metabolic, and thermoregulatory aggressions. These roles are made possible due to a complex structure that brings together varied tissue structures. The skin, as well as the hair and nails, is constantly subjected to external pollution, which manifests under different aspects. These aggressions can be significant and threaten the equilibrium and appearance of the skin. Examples of aggressors include visible light and UV rays, atmospheric pollutants, chemical products, mechanical stressors, and bacterial or viral infections.

The skin is our first barrier against the external environment. However, this barrier is not always sufficient and these aggressions can have numerous negative consequences for the organism and the cells.

The skin cells, in direct contact with the external environment, encounter damage in a variety of ways, and, in particular, experience an alteration in their macromolecules. We can mention, for example, damage caused to DNA (such as simple or double strand, mutations, etc.), damage caused to proteins (protein carbonylation, etc.), and modifications of fatty acids (lipid peroxydation, etc.), all of which result in cell membrane damage and impairments of the cutaneous barrier.

These damages occur on all types of cutaneous cells, but we can mention in particular keratinocytes, fibroblasts and melanocytes. External aggressions often have visible consequences including early skin aging, depigmentation, and inflammatory reactions. They can even lead to cancer development and tissue necrosis.

Therefore, it is important to develop systems capable of fighting actively against these aggressions and their consequences. A great number of researchers, particularly in the field of cosmetics, have been mobilized to search for a means to preserve the skin, nails, and hair, and even to protect them against all signs likely to impair their healthy functioning and appearance.

Cosmetic and health professionals are constantly searching for high-performance active ingredients that are very efficient and have a wide range of action. Moreover, the active ingredients must have a high dermatological compatibility so that no irritation is experienced by any of the individuals who use them, even the most sensitive ones. There remains the need to develop dermatological and/or cosmetic active ingredients that offer high efficiency as well as a wide range of applicability for the hair and nails.

The applicants have recently discovered the involvement of a new protein in the mechanisms of skin cells which has a significant role in the aging process and cell protection.

The applicants have demonstrated that the SIRT protein, and more precisely the SIRT1 protein, was expressed in skin cells and that its expression was related to different stresses that cutaneous cells encounter. They have demonstrated in particular that the induction of this protein expression, using different agents, allowed for the protection of cells and better helped them to fight against stress and intrinsic aging.

SIRT proteins are part of the Sirtuin family, and are NAD+ dependent nuclear proteins that play a significant role in histone deacetylation. SIR genes (Silent Information Regulators), which code for SIR proteins, were described for the first time in *S. cerevisiae* in 1979 (Rine J and A l., *Genetics* 1979). Later, it was demonstrated that an over-expression of the SIR2P protein, in *C. elegans*, allowed the lifespan of the organism to increase (Tissenbaum and A l., *Nature* 2001). This study has permitted to hypothesize that these proteins are related to longevity.

The SIRT1 protein is the best characterized human sirtuin and interacts with numerous transcription regulators. The human SIRT1 protein has been described as being involved in p53 regulation (Cheng H L and Al. *Proc Natl Acad Sci USA*. 2003), and more recently as a modulator of cell senescence (Langley E and Al., *EMBO J.* 2002). Other human SIRT proteins have been discovered (SIRT2, SIRT3, SIRT4-7). The human SIRT2 protein has been studied very little; however some studies have demonstrated its role in the control of mitotic activity (Dryden S C and Al. Mol Cell Bio. 2003) as well as its involvement in the regulation of the p53 protein (Vaziri H and Al., Cell. 2001). To date, deacetylase sirtuins are considered a family of enzymes playing an important role in the regulation of cellular death and in its lifecycle (Porcu M. and Chiarugi A, *Trends Pharmacol Sci.,* 2005).

The present invention relates to a cosmetic or pharmaceutical composition comprising, in a cosmetically or pharmaceutically acceptable medium, at least one compound likely to activate the synthesis of SIRT proteins in skin cells. Preferentially, according to the invention, the compounds will activate a particular class of SIRT proteins, the SIRT1 proteins.

To date, no use of compounds that serve as inductors of the synthesis of the SIRT family of proteins, in skin cells, has ever been described.

With a compound likely to activate SIRT protein synthesis in skin cells, it is primarily intended to indicate all the compounds likely to support the endogenous production of SIRT proteins, particularly the molecules involved in the positive control of precursors such as DNA or RNA.

Among these compounds, which are likely to activate the synthesis of SIRT proteins in skin cells, different molecules, such as polyphénols, has been described. More particularly derivatives of trans-stilbene (resveratrol, piceatannol), derivatives of chalcones (isoliquiritigenin, butein), and derivatives of flavones (fistein, luteolin, quercetin) can be mentioned.

Preferentially, according to the invention, the compounds likely to activate the synthesis of SIRT proteins in skin cells will be compounds of peptidic nature.

Among the compounds of peptidic nature, protein fragments, peptidic and polypeptidic fragments, peptides, as well as all sequences of two or more amino acids linked together by peptide bonds can be mentioned. In a preferred embodiment of the present invention, said peptide fragments are peptide fragments ranging in size from 3 to 50 amino acids, more particularly from 3 to 10 amino acids. All of these peptide fragments have a biological activity.

According to a particularly advantageous embodiment of the invention, the compound, likely to activate the synthesis of SIRT proteins of the skin, is a peptide of sequence (I):

(SEQ ID NO: 1)
(I) (AA)n-Gly-Leu-Tyr-Asp-Asn-Leu-Glu-(AA)n wherein (AA) is any particular amino acid or derivative thereof, and n is a whole number and ranges between 0 and 3.

Moreover, according to a preferred embodiment of the invention, the compound, an inductor of the SIRT proteins of the skin, has the sequence Gly-Leu-Tyr-Asp-Asn-Leu-Glu (SEQ. ID NO: 2).

The phrase "SIRT proteins of the skin" refers to all the proteins of the SIRT family, but preferentially, refers to SIRT1 proteins.

The invention also relates to variant forms of these sequences and/or of these fragments. The expression "variant" indicates a polypeptide or a peptide that differs, for example, from the sequence of a reference peptide while keeping its essential properties. Generally, the differences are limited so that the sequences of the reference peptide and those of the variant are quite similar and, in some regions, identical. A variant peptide and a reference peptide may differ in their amino acid sequence by one or several substitutions, additions, or deletions in all the combinations. Preferentially, the variant forms are those which vary from reference sequences, by the substitution of chemically equivalent (or homologous) amino acids, that is, by the substitution of a residue by another possessing the same characteristics. Thus, the classical substitutions take place between Ala, Val, Leu and Ile; between Ser and Thr; between the acid residues Asp and Gln; and between the basic residues Lys and Arg, or between the aromatic residues Phe and Tyr.

In the invention, the expression "amino acid" refers to any natural or unnatural organic acid having the formula:

—NHR—CR—C(O)—O— where each —R is independently selected from a hydrogen or an alkyl group having between 1 and 12 carbon atoms. Preferentially, at least an —R group of each amino acid is a hydrogen. The term "alkyl" refers to a carbon chain that can be linear or branched, substituted (mono- or poly-) or not substitute; saturated, mono-saturated (a double or triple bond in the chain), or poly-unsaturated (two or several double bonds, two or several triple bonds, one or several double bonds, and one or several triple bonds in the chain).

The term "peptide" indicates a sequence of two or several amino acids linked together by peptide bonds or by modified peptide bonds; and a polypeptide indicates a peptide of larger size. The term "peptide" refers to a natural or synthetic peptide of the invention as described above or at least any natural or synthetic peptide whose sequence is totally or partly constituted by the sequence previously described.

It may be that, concerning issues of resistance to degradation, it is necessary to use a protected form of the peptide according to the invention. The form of protection must obviously be biologically compatible and must be compatible with the use in the cosmetic and pharmaceutical fields.

Many biologically compatible forms of protection can be considered, such as the acylation or the acetylation of the N-terminal amine group, or the amidation or esterification of the terminal carboxyl group. Such forms are well known to one skilled in the art. Thus, the invention relates to the use as previously defined and is characterized by the fact that the peptide either is or is not in a protected form. Preferably, the protection used is either the acylation or the acetylation of the N-terminal amine group, or the esterification or the amidation of the terminal carboxyl group, or both of them. The amino acid derivatives and the peptide derivatives also relate to the amino acids and peptides bound together by a pseudo-peptide bond. By the term "pseudo-peptide bond," we refer to all types of bonds likely to replace the "classical" peptide bonds.

In the field of amino acids, the geometry of the molecules is such that they can be theoretically presented as different optical isomers. There is indeed a molecular conformation of the amino acid (AA) such that it deviates to the right of the plane of polarization of the light (dextrorotatory conformation or D-aa), and a molecular conformation of the amino acid (aa) such that it deviates to the left of the plane of polarization of the light (levorotatory conformation or L-aa). Nature retained for the natural amino acids only levorotatory conformation. Consequently, a peptide of natural origin will be made up only of amino acids of type L-aa. However, chemical synthesis in a laboratory makes it possible to prepare amino acids having two possible conformations. From this basic material, it is thus possible to incorporate, during peptide synthesis, amino acids in the form of dextrorotatory or levorotatory optical isomers. Thus, the amino acids constituting the peptide according to the invention, can be under configuration L- and D-; in a preferential way, amino acids are in L configuration. The peptide according to the invention can be in L, D, or DL-configuration.

According to the invention, the peptides can be prepared using all appropriate methods. Thus, the peptides can be isolated peptides from peptides and proteins existing naturally, recombinant peptides, synthetic peptides, or peptides produced by a combination of these methods. Of course, the methods, in order to prepare the peptides according to the invention, are well know by one skilled in the art. Thus, the peptide according to the invention may be of natural or synthetic origin. Preferentially, according to the invention, the peptide is obtained by chemical synthesis.

It is evident that the compounds likely to activate the synthesis of SIRT proteins in skin cells will be used alone or in combination with at least another active agent, in or for the preparation of a cosmetic, and/or dermatological, and/or pharmaceutical composition.

According to an advantageous mode of embodiment of the invention, the above mentioned compounds are solubilized beforehand in one or several solvents cosmetically or pharmaceutically acceptable, classically used by one skilled in the art, such as water, ethanol, propylene glycol, butylene glycol, dipropylene glycol, ethoxylated or propoxylated diglycols, cyclic polyols, vaseline, a vegetal oil, or any combinations of these solvents.

According to another advantageous embodiment of the invention, the compounds abovementioned are solubilized beforehand in one cosmetic or pharmaceutical vector such as liposomes or adsorbed on powdery organic polymers, mineral supports like talcs and bentonites, and more generally solubilized in, or linked to any vector compatible with use in the cosmetic or pharmaceutical fields.

The composition, containing the compounds likely to activate the synthesis of SIRT proteins in skin cells, may be a dermatological or pharmaceutical or cosmetic composition.

The composition, according to the invention, can be a cosmetic, dermatological, or pharmaceutical composition. Preferentially, according to the invention, the composition is a cosmetic composition, because it is intended to improve the appearance and the general cutaneous performances of the skin.

The composition, according to the invention, is preferentially a cosmetic and/or a dermatological composition, appropriate for topical administration on the skin, and includes a medium compatible with use in the cosmetic or pharmaceutical fields. Preferentially, according to the invention, the composition is a cosmetic composition; it is intended to improve the appearance and general cutaneous performances of the individual who uses it.

The effective amount of active ingredient corresponds to the necessary amount in order to obtain the desired result. According to the mode of embodiment of the invention, the above mentioned compounds are present in the composition of the invention in an amount between around $10^{-6}$ and 20%, and preferentially in an amount between about $10^{-4}$ and 5% with respect to the total weight of the final composition.

Whatever form the invention takes, the composition, according to the invention, can be injected or applied to the skin (to all cutaneous areas of the body), hair, nails, or mucous membranes. According to the mode of administration, the composition related to the invention can be presented under all galenic forms normally used.

Preferentially, the compositions related to the invention are presented under a galenic form adapted for cutaneous topical administration. They cover all the cosmetic and dermatological forms. These compositions must contain an acceptable cosmetic or dermatological medium. That is to say, a medium that is compatible with skin, mucous membranes, hair, and nails.

These compositions can take the form of an aqueous, hydro-alcoholic or oil solution; or the form of oil-in-water, water-in-oil emulsions, or in multiple emulsions. They can also be used as creams, as a suspension or as a powder, adapted for application to the skin, mucous membranes, lips, and/or hair and nails. These compositions can also be more or less fluid or solid and can take the form of creams, lotions, milks, serums, ointments, shampoos, gels, pastes, and mousse. They can also take a solid form like a stick, or they can be used on the skin or in aerosols. They can also be used as a skin care product and/or as make-up for skin.

Moreover, these compositions can include all of the additives that are usually considered for use in this application including all the possible additives necessary for their formulation such as solvents, thickeners, diluents, antioxidants, colorants, solar filters, auto-tanning products, pigments, fillers, preservatives, perfumes, odor absorbers, pharmaceutical and cosmetic active ingredients, essential oils, vitamins, essential fatty acids, tensioactivators, filmogen polymers, etc.

In all cases, one skilled in the art will attempt to carefully consider the selection of additives, as well as their proportions, so as not to compromise the advantageous properties of the composition relating to the invention. These additives can, for example, correspond to 0.01% to 20% of the total weight of the composition. When the composition according to the invention is an emulsion, the fatty phase can represent 5% to 80% of the weight, but preferably it would represent 5% to 50% of the weight with respect to the total weight of the composition. Emulsifiers or co-emulsifiers used in the composition will be selected from among those that are classically used in the domain under consideration. For example, they can be used in a proportion of 0.3% to 30% of the weight relative to the total weight of the composition. Of course, the person skilled in the art should select the complementary compounds for the composition, active or non-active, as well as the amounts of the complementary compounds in such a way that the advantageous properties of the composition will not be perceptibly altered by the envisioned addition.

The compositions, according to the present invention, can be applied most notably as a cosmetic or pharmaceutical composition for use on the skin, mucous membranes, and/or semi-mucous membranes. The compositions can be applied as skin protection and/or as skin care products, or as an anti-wrinkle and/or an anti-aging composition. We can also envision other applications in the domain of combined compositions for example, with other active agents. We can also use the compounds according to the invention in the cosmetic compositions for body and hair health.

The recent discovery of the presence of SIRT proteins in skin cells, and particularly the presence of SIRT1 protein, as well as their involvement in many fundamental cell mechanisms, and notably, those involved in cell stress, allowed to envisage multiple uses for the compounds according to the invention. The SIRT1 protein plays a very significant function in aging and cell protection. Indeed, it has been demonstrated that an increase of its expression enables the skin to better resist surrounding stress, and that it is more able to combat oxidation process, and more generally, to better combat aging. More globally, inducing expression of this protein in skin cells brings a general improvement of the mechanisms of cell protection and could increase cell life span.

Several uses of the previously defined compounds, intended to activate the endogenous synthesis of SIRT proteins, and in particular, SIRT1 proteins, or of compositions containing them, have therefore been envisioned. Thus, an essential aspect of the invention is the use of at least one inducer compound of the endogenous synthesis of SIRT proteins in skin cells, in or for the preparation of a cosmetic and/or pharmaceutical composition, the compound or the composition containing it being intended to bring care to skin and/or hair and/or nails.

More precisely, among the inducer compounds of the endogenous synthesis of SIRT proteins, we can mention compounds of peptidic nature. Preferentially, the compounds likely to activate the synthesis of SIRT proteins, and particularly of SIRT1 proteins, will be peptides corresponding to the sequence (I). According to a preferred method of embodiment of the compound, the inductor of the SIRT proteins of the skin, has the sequence:

(SEQ ID NO: 2)
Gly-Leu-Tyr-Asp-Asn-Leu-Glu.

The aforementioned compounds, being used advantageously in order to combat, in a curative and/or preventative way, the signs of cutaneous aging, are also used in order to improve the appearance of keratinous substrates.

The expression "care of the keratinous substrates" refers to all the actions intended to preserve or restore the healthy functioning of skin and/or hair and/or nails or any process providing the means to preserve or improve their appearance and/or texture. Thus, care includes hydration, appeasement, protection against all types of aggression, notably sun protection, and fighting against and preventing the signs of aging. The phrase "signs of cutaneous aging" includes all of the modifications regarding external appearance of skin due to aging. Examples of these modifications include wrinkles and fine lines, limp skin, slackened skin, thin looking skin, loss of elasticity and/or skin tone, dull skin, and skin which lacks radiance. It also includes internal skin modifications that do not translate directly as changes in external skin appearance. An example of these internal modifications is the degradation that occurs internally in skin resulting from consecutive exposure to UV radiation. The expression "to enhance skin appearance" includes all the phenomena which are likely to have as consequences a visual improvement of skin appearance. The skin will have a nicer look; it will be, for example, much more beautiful, firm, and/or smooth. All the small imperfections will be decreased or removed. The papery appearance of the skin, for example, will be attenuated.

Moreover, the active ingredient according to the invention, or the composition containing it, can be intended to protect keratinous substrates and, particularly, the skin, hair, and nails from all types of external aggression. The use of these active agents, or the composition containing them, will allow the keratinous substrates to be protected and to better resist stress inflicted upon them by the environment.

The phrase "external aggression" refers to aggressions produced by the environment. These can be of chemical, physical, biological, or thermic origin.

According to another aspect, the compounds will be used in an advantageous way in order to diminish and/or prevent cutaneous inflammatory and/or anti-irritating reactions. The use of these active agents allow the skin to have better protection and much less sensitivity to various aggressions it may encounter. In this way, the skin is appeased.

Moreover, the compounds according to the invention, such as previously defined, stimulate the metabolic functioning of skin cells. They allow protein synthesis to increase, which is essential for its functioning, notably by increasing the synthesis of constitutive proteins of the extracellular matrix. The compounds, according to the invention, or the composition containing them, thus have a positive action on tissue regeneration. The compounds according to the invention are particularly efficient in order to treat wound-healing disorders.

The compositions, intended to activate the endogenous synthesis of SIRT proteins, previously defined, are used in or for the manufacture of pharmaceutical and/or cosmetic compositions, for topical use. They will be used, in a more general way, in order to treat dermatological disorders.

The expression "dermatological disorder" refers to all the diseases affecting the skin that may or may not have visible consequences. Therefore, by way of example: differentiation and cell proliferation disorders, keratinization disorders, inflammatory or allergic reactions, disorders of sebaceous functions, dermal or epidermal proliferations (malignant or non-malignant), cutaneous disorders due to UV ray exposure, and pathologies associated with chronological or actinic aging can be mentioned.

Moreover, according to another aspect, compounds previously defined according to the invention, intended to activate the endogenous synthesis of SIRT proteins in skin cells, are used for the manufacture of a medicament for the treatment of dermal conditions. The present invention also relates to the use of the compounds previously defined as medicaments.

Moreover, according to another aspect, the present invention relates to a cosmetic process of treatment for skin care and/or hair and nail care consisting of applying, to the surface of the skin, an effective amount of the active agent, such as previously defined, in order to obtain the desired action. The processes can notably be used in order to treat in a curative and/or preventive manner the signs of cutaneous aging, but also to protect the skin and/or hair and/or nails from external aggressions such as negative effects of radiation, and in particular UV radiation, or in order to combat the signs of cutaneous inflammation and irritation.

The process of cosmetic treatment related to the invention can be implemented notably by applying the cosmetic compositions defined above according to methods usually used for compositions, such as the application of creams, gels, serums, lotions, milks, shampoos, and sun protection creams, on skin or hair, and as a toothpaste applied to the gums.

Particular modes of embodiment of this cosmetic treatment process also result from the preceding description. Other advantages and characteristics of the invention will become apparent by reading the following illustrative and unrestrictive examples.

EXAMPLE

Preparation of Compositions

The mentioned amounts are given as a percentage of the weight.

1—Anti-Wrinkle Care Cream:

| INCI names | % by weight |
| --- | --- |
| PHASE A | |
| Cetearyl Alcohol (and) Cetearyl Glucoside | 6.00 |
| Squalane | 3.00 |
| *Butyrospermum Parkii* (Shea Butter) | 2.00 |
| Cetearyl Ethylhexanoate | 3.00 |
| Mineral Oil (and) Lanolin Alcohol | 2.00 |
| Dimethicone | 1.50 |
| BHT | 0.01 |
| PHASE B | |
| Water (Aqua) | qs |
| Butylene Glycol | 2.00 |
| Methyl Gluceth-10 | 1.00 |
| Allantoin | 0.15 |
| Carbomer | 0.20 |
| PHASE C | |
| *Persea* Gratissima (Avocado) Oil | 1.25 |
| Phenoxyethanol (and) Methylparaben (and) Ethylparaben (and) Butylparaben (and) Propylparaben (and) Isobutylparaben | 0.75 |
| PHASE D | |
| Triethanolamine | 0.18 |
| PHASE E | |
| Peptide according to the invention | 2 ppm |
| Fragrance | qs |

The constituents of phase A and phase B are heated separately at a temperature ranging from 65° C. to 70° C., phase C is incorporated, then phase A is emulsified in phase B. Carbomer is neutralized in phase D at a temperature of about 45° C. Phase E is then added under agitation and cooling is pursued down to 25° C.

2—Anti-Aging Body Milk:

| Noms INCI | % massique |
| --- | --- |
| PHASE A | |
| Water (Aqua) | qs |
| Acrylates/C10-30 Alkylacrylate Crosspolymer | 0.10 |
| Glycerin | 1.20 |
| Trisodium EDTA | 0.65 |
| Propylene Glycol | 1.50 |
| PHASE B | |
| Caprylic/Capric Triglyceride | 2.50 |
| Mineral Oil (and) Lanolin Alcohol | 2.00 |
| Squalane | 1.50 |
| Cetearyl Isononanoate | 2.00 |
| Stearic Acid | 2.00 |
| Glyceryl Stearate SE | 3.00 |

| Noms INCI | % massique |
|---|---|
| Cetyl Alcohol | 0.20 |
| Dimethicone | 0.50 |
| Phenoxyethanol (and) Methylparaben (and) Ethylparaben (and) Butylparaben (and) Propylparaben (and) Isobutylparaben | 0.70 |
| PHASE C | |
| Triethanolamine | 0.08 |
| PHASE D | |
| Peptide according to the invention | 0.5 ppm |
| Fragrance | qs |
| colorant | qs |

The constituents of phase A and phase B are heated separately at a temperature ranging from 70° C. to 75° C. Phase B is emulsified in phase A under "Staro" agitation. After cooling down to 50° C., the mixture is neutralized in phase C. Phase D is then added when the temperature is below 40° C. Cooling is pursued down to 25° C. under slow agitation.

3—Sun Cream Protection:

| Noms INCI | % massique |
|---|---|
| PHASE A | |
| Water (Aqua) | qs |
| Acrylates/C10-30 Alkyl Acrylate | 0.40 |
| Crosspolymer | |
| Glycerin | 3.00 |
| Sodium Methylparaben (and) Sodium Ethylparaben (and) Sodium Butyl paraben (and) Sodium Propylparaben (and) Sodium Isobutylparaben | 0.15 |
| PHASE B | |
| Ethylhexyl Methoxycinnamate | 7.50 |
| Benzophenone-3 | 3.00 |
| Butyl Methoxydibenzoylmethane | 2.00 |
| Caprylic/Capric Triglyceride | 4.00 |
| Hydrogenated Palm Glycerides (and) Ceteareth-20 (and) Ceteareth-12 (and) Cetearyl Alcohol | 5.00 |
| Propylparaben | 0.15 |
| Cetyl Alcohol | 1.00 |
| PHASE C | |
| Triethanolamine | 0.20 |
| Peptide according to the invention | 1 ppm |
| Fragrance | qs |
| colorant | qs |

The constituents of phase A and phase B are heated separately at a temperature ranging from 70° C. to 75° C. Phase B is emulsified in phase A under agitation. Phase C is added, at 45° C., increasing the agitation. Phase D is then added when the temperature is below 40° C. Cooling is pursued down to 25° C. under strong agitation.

The invention claimed is:

1. A method for non-therapeutic care intended to improve appearances and general cutaneous performance of skin, comprising:
administering to the skin an effective amount of at least one compound able to activate endogenous synthesis of sirtuin (SIRT1) protein, wherein the compound is a peptide of sequence (I): (AA)n-Gly-Leu-Tyr-Asp-Asn-Leu-Glu-(AA)n (AA) is any particular amino acid, and n is a whole number and ranges from 0 to 3.

2. A method to protect skin, against negative effects of UVB radiation, comprising:
administering to the skin an effective amount of at least one compound able to activate endogenous synthesis of sirtuin (SIRT1) protein, wherein the compound is a peptide of sequence (I): (AA)n-Gly-Leu-Tyr-Asp-Asn-Leu-Glu-(AA)n, (AA) is any particular amino acid, and n is a whole number and ranges from 0 to 3.

3. The method according to claim 1, wherein the compound is a peptide of sequence Gly-Leu-Tyr-Asp-Asn-Leu-Glu.

4. The method according to claim 1, wherein the compound is administered in the form of a composition containing cosmetically or pharmaceutically acceptable excipients.

5. The method according to claim 4, wherein the excipients are adapted to an external topical administration.

6. A cosmetic or pharmaceutical composition wherein, in a cosmetically or pharmaceutically acceptable medium, at least one compound is able to activate the synthesis of sirtuin (SIRT1) protein in skin cells, wherein the compound is a peptide of sequence (I): (AA)n-Gly-Leu-Tyr-Asp-Asn-Leu-Glu-(AA)n, (AA) is any particular amino acid, and n is a whole number and ranges from 0 to 3.

7. The composition according to claim 6, wherein the medium is adapted to an external topical administration.

8. The composition according to claim 6, wherein the compound is a peptide of the sequence Gly-Leu-Tyr-Asp-Asn-Leu-Glu.

9. The composition according to claim 6, wherein said compound, able to activate the synthesis of SIRT1 protein, is present in an amount between about $10^{-6}$ and 20% with respect to the total weight of the final composition.

10. The composition according to claim 6, wherein the compound is present in the composition at a concentration ranging from about 0.05 ppm to about 500 ppm with respect to the total weight of the final composition.

11. A process or method for treating the signs of cutaneous aging, comprising applying on keratinous substrates a cosmetic composition according to claim 6.

12. The composition according to claim 9, wherein the compound is present in an amount between about $10^{-4}$ and 5% with respect to the total weight of the final composition.

13. The composition according to claim 10, wherein the compound is present, at a concentration ranging from about 0.1 ppm to about 50 ppm with respect to the total weight of the final composition.

* * * * *